(12) United States Patent
Zendejas-Martinez (10) Patent No.: US 10,927,424 B2
(45) Date of Patent: Feb. 23, 2021

(54) METHOD AND SYSTEM FOR PRODUCING HIGH-CARBON DRI USING SYNGAS

(71) Applicants: HYL TECHNOLOGIES, S.A. DE C.V., Nuevo Leon (MX); DANIELI & C. OFFICINE MECCANICHE S.p.A., Buttrio (IT)

(72) Inventor: Eugenio Zendejas-Martinez, Monterrey (MX)

(73) Assignees: HYL TECHNOLOGIES, S. A. DE C.V., Nuevo Leon (MX); DANIELI & C. OFFICINE MECCANICHE S.P.A., Buttrio (IT)

(*) Notice: Subject to any disclaimer, the term of this patent is extended or adjusted under 35 U.S.C. 154(b) by 299 days.

(21) Appl. No.: 16/063,604

(22) PCT Filed: Dec. 21, 2016

(86) PCT No.: PCT/IB2016/001917
§ 371 (c)(1),
(2) Date: Jun. 18, 2018

(87) PCT Pub. No.: WO2017/115133
PCT Pub. Date: Jul. 6, 2017

(65) Prior Publication Data
US 2018/0371560 A1 Dec. 27, 2018

Related U.S. Application Data

(60) Provisional application No. 62/271,970, filed on Dec. 28, 2015.

(51) Int. Cl.
*C21B 13/00* (2006.01)
*C21C 7/00* (2006.01)
(Continued)

(52) U.S. Cl.
CPC ...... *C21B 13/0013* (2013.01); *C21B 13/0066* (2013.01); *C21B 13/0073* (2013.01);
(Continued)

(58) Field of Classification Search
CPC ............ C21B 13/0013; C21B 13/0066; C21B 13/0073; C21B 2100/282; C21B 2100/24;
(Continued)

(56) References Cited

U.S. PATENT DOCUMENTS 3,904,386 A * 9/1975 Graboski .............. C07C 1/0485
48/197 R
5,387,274 A * 2/1995 Dam G. .................. C21B 13/04
75/495
(Continued)

FOREIGN PATENT DOCUMENTS

CN 102712959 10/2012
WO WO 00/036158 6/2000
(Continued)

OTHER PUBLICATIONS

Berger et al. ("Comparing physisorption and chemisorption solid sorbents for use separating CO2 from flue gas using temperature swing adsorption." Energy Procedia 4 (2011): 562-567.) (Year: 2011).*
(Continued)

*Primary Examiner* — Anthony J Zimmer
*Assistant Examiner* — Ricardo D Morales
(74) *Attorney, Agent, or Firm* — Fish & Richardson P.C.

(57) ABSTRACT

Producing direct reduced iron (DRI) having chemically-combined carbon includes providing DRI at a temperature above 400° C., providing a first gas stream including hydrogen and carbon monoxide, passing the first gas stream through a methane forming process to yield a second gas stream containing a higher concentration of methane than
(Continued)

the first gas stream; and contacting the second gas stream with the DRI. A system for producing the DRI includes a vessel for containing DRI at a temperature above 400° C., a methane forming reactor containing a catalyst bed for producing methane from a first gas stream containing hydrogen and carbon monoxide, a first conduit to feed a gas stream including hydrogen and carbon monoxide to the methane forming reactor, and a second conduit to feed the second gas stream to the vessel containing the DRI.

26 Claims, 2 Drawing Sheets

(51) Int. Cl.
    *C01B 32/40*     (2017.01)
    *C01B 32/935*     (2017.01)
    *C01B 3/34*     (2006.01)
    *C07C 9/04*     (2006.01)

(52) U.S. Cl.
    CPC .............. *C21C 7/0025* (2013.01); *C01B 3/34* (2013.01); *C01B 32/40* (2017.08); *C01B 32/935* (2017.08); *C01B 2203/0283* (2013.01); *C07C 9/04* (2013.01); *C21B 2100/24* (2017.05); *C21B 2100/282* (2017.05); *Y02P 10/122* (2015.11); *Y02P 10/134* (2015.11); *Y02P 10/143* (2015.11)

(58) Field of Classification Search
    CPC .... C21C 7/0025; Y02P 10/122; Y02P 10/126; Y02P 10/136; Y02P 10/143; C01B 32/40; C01B 32/935; C01B 3/34; C01B 2203/0283; C07C 9/04
    See application file for complete search history.

(56) References Cited

U.S. PATENT DOCUMENTS

| | | |
|---|---|---|
| 8,496,730 B2 | 7/2013 | Metius et al. |
| 9,127,326 B2 | 9/2015 | Metius et al. |

FOREIGN PATENT DOCUMENTS

| | | |
|---|---|---|
| WO | 2011/012964 | 2/2011 |
| WO | WO 2017/115133 | 7/2017 |

OTHER PUBLICATIONS

Er-rbib et al. ("Methanation catalytic reactor." Comptes Rendus Chimie 17.7-8 (2014): 701-706).) (Year: 2014).*
PCT International Search Report for PCT Application No. PCT/IB2016/001917 filed Dec. 21, 2016; dated May 8, 2017, 4 pages.
Written Opinion of the International Searching Authority for PCT Application No. PCT/IB2016/001917 dated May 8, 2017, 6 pages.

* cited by examiner

METHOD AND SYSTEM FOR PRODUCING HIGH-CARBON DRI USING SYNGAS

CLAIM OF PRIORITY

This application claims priority under 35 USC § 120 to PCT Patent Application Serial No. PCT/IB2016/001917 filed on Dec. 21, 2016, which claims priority under 35 USC § 119 to U.S. Provisional Application Ser. No. 62/271,970 filed on Dec. 28, 2015, the entire contents of both of which are incorporated herein by reference.

FIELD OF THE INVENTION

The present invention relates generally to systems and methods for producing high-carbon metallic-iron-containing materials (known as sponge iron, direct reduced iron or DRI) in a direct reduction reactor system using a syngas derived from gasification of hydrocarbons. More particularly, the present invention involves the modification of the composition of a portion of a reducing gas stream of the direct reduction reactor system to increase its methane content sufficiently to produce an effective carburizing gas stream which is fed to the reduction reactor to produce said high-carbon DRI.

BACKGROUND OF THE INVENTION

High-carbon DRI is more and more attractive to the steelmakers due to the advantages resulting from use of this product in electric arc furnaces.

The present invention provides a practical and economic solution to produce high-carbon DRI, when the source of reducing gas is a high-temperature coal gasifier, or a similar syngas producer, that provides a synthesis gas comprising a mixture of hydrogen and carbon monoxide but has a very low methane content (insufficient to yield the desired high-carbon DRI).

The term "high-carbon DRI" is here understood to be DRI containing more than 2% chemically combined carbon by weight.

The technologies for direct reduction of iron ores, since their origin, have been typically based on the use of natural gas. This is a relatively clean source of hydrocarbon gas, mostly methane, and usually contains from about 80% to 95% methane. Due to the availability of natural gas in many regions, it may be extracted along with oil in oil fields, or more recently, from vast shale deposits. It has been used as a source of energy for power production, as raw material for production of a variety of chemical products and for direct reduction of iron oxides to metallic iron. Coke Oven Gas, a by-product of the manufacture of metallurgical coke, may also be used as a source of reducing gases in those regions where natural gas is not available.

Production of DRI is carried out in the solid state by reacting iron-bearing materials (iron oxides) with a reducing gas at high temperature. The reducing gas is a mixture of hydrogen and carbon monoxide in a wide range of proportions depending on the process used to transform the hydrocarbons (mainly methane) contained in the natural gas. Most of the direct reduction plants in operation utilize a reformer where the hydrocarbons react with oxidants, namely $CO_2$ and $H_2O$, or only $H_2O$, at high temperature, over 750° C., in the presence of a catalyst. Reformers are operated so that the conversion of methane to $H_2$ and CO is maximized, so that the investment and operating costs of such reformers are economically sound for a given capacity of DRI production.

There are also direct reduction plants operating without such reformers wherein the reducing gases $H_2$ and CO are produced within the reduction system taking advantage of the catalytic effect of the DRI present in the reduction reactor. In this case, the methane content fed to the reduction reactor is much higher, in the order of 15% to 20% in volume, as compared to the methane content of the reducing gas fed to the reduction reactor when the $H_2$ and CO are produced in a reformer or in a high-temperature hydrocarbon gasifier, which is on the order of 1% to 5% by volume, as disclosed in U.S. Pat. Nos. 5,858,057 and 6,039,916.

DRI is carburized mainly one of two chemical reactions: (a) by high temperature cracking of a hydrocarbon, typically $CH_4$, at a temperature above 400° C. which produces elemental carbon and $H_2$; and (b) by reaction of CO with $H_2$ to produce elemental carbon and $H_2O$, according to the following reactions:

$$CH_4 \rightarrow C+H_2 \quad (a)$$

$$CO+H_2 \rightarrow C+H_2O \quad (b)$$

The following reaction also occurs minimally:

$$2CO \rightarrow C+CO_2 \quad (c)$$

The resulting elemental carbon combines with metallic iron to produce $Fe_3C$:

$$C+3Fe \rightarrow Fe_3C \quad (d)$$

The operative results of the above reactions (a) and (b) in practice are very different in their effectiveness.

Reaction (a), i.e. using $CH_4$ as the source of carbon, requires temperatures above about 700° C. to crack the $CH_4$ molecule and a concentration above about 10% by volume of $CH_4$ in the gases within the reduction reactor, or in a separate DRI carburizing vessel.

Since methane is available in natural gas, which is also used to produce the reducing gas for reduction of the iron oxides, or similarly in coke oven gas which is available in many integrated steel plants; the generalized method to produce DRI with combined carbon is to feed natural gas to the transition zone or the cooling zone of a moving bed reactor (as proposed for example in U.S. Pat. Nos. 4,054,444; 4,752,329; 4,702,766; and 5,078,787). This $CH_4$ reaction occurs simultaneously with the reduction reactions of $H_2$ and CO in the reduction zone of a reduction reactor if the $CH_4$ concentration in the reducing gas is sufficiently high.

U.S. Pat. No. 7,854,786 is concerned with the need for better direct and complete control of the carburizing phase process when using syngas. To achieve its goal for better control, this patent requires an additional step "to separate the methane from the rest of the components" of "a portion or all of the syngas.". However, the amount of $CH_4$ available to carburize the DRI remains the same amount which is contained in the external syngas source 11, which is low. The present invention in contrast increases, as needed, the $CH_4$ available for carburization independently of the $CH_4$ content of the syngas 11. There is no discussion of, or any concern expressed about, any need to increase the methane content of the syngas 11 (much less any mention of the specific degree of methane content of the syngas 11 used or how to increase the amount of methane needed for the purpose of increasing the carbon content of the DRI produced).

CO is present in the reducing gas used for reduction of iron oxides, and therefore reaction (b) occurs to some degree simultaneously with the reduction reactions, but has the disadvantage that the thermodynamic equilibrium is displaced to CO at high temperatures. Consequently, the degree of conversion of CO to C essentially occurs at temperatures below about 700° C. and lower. Therefore, the carbon deposition is low at the conditions of the reduction zone of the reduction reactor and it is not sufficiently effective even at the lower temperature of the transition zone and the cooling zone of the reduction reactor.

Producing DRI with high carbon content therefore is readily achievable when natural gas or coke oven gas are available as sources of $CH_4$ (including some heavier gaseous hydrocarbons as $C_2H_6$, $C_3H_8$, including some aromatic compounds), but to the best of our knowledge it has not previously been done when the source of reducing gas is a syngas with a low content of $CH_4$. This situation is important in those regions where coal is gasified to produce syngas using partial oxidation of coal where all the hydrocarbon compounds of coal are cracked and decomposed by the reaction with oxygen and/or steam and destroy even the $CH_4$ molecules to produce a syngas with a high content of CO, $H_2$ and $CO_2$ among other compounds. This syngas typically has less than about 2% of $CH_4$.

The advantages provided by the high-carbon DRI at the steelmaking furnace are many and therefore there is a yet unfulfilled need in the steelmaking industry to provide a DRI process and system that produces DRI with a controlled amount of combined carbon, above about 2% by weight that enables use of a syngas with low content of $CH_4$, lower than about 5% by volume.

There are many proposals in the prior art to produce DRI with high carbon content, mostly in the form of $Fe_3C$, i.e. chemically combined with iron, as opposed to producing soot, that is free carbon over the DRI. These use gases containing high concentration of methane, such as natural gas and coke oven gas, but none have utilized syngas of low $CH_4$ content derived from solid or liquid hydrocarbon gasifiers.

The present invention provides systems and methods to produce DRI with high carbon content by producing a methane-rich DRI-carburizing gas from a syngas having $H_2$, CO, $CO_2$ and a low $CH_4$ content by reacting the CO and $CO_2$ with $H_2$ in an isothermic or an adiabatic catalytic reactor (methanator) whereby a methane-rich gas is formed according to the following methanation reactions:

(e)

(f)

An example of an adiabatic methanation process is disclosed in U.S. Pat. No. 4,130,575, and an example of an isothermic methanation process is described in U.S. Pat. No. 5,869,011 and an example of a methanation process combining both isothermic and adiabatic reactors is shown in U.S. Pat. No. 4,294,932.

Documents cited in this text (including the patents discussed herein), and all documents cited or referenced in the documents cited in this text, are incorporated herein by reference. Documents incorporated by reference into this text or any teachings therein may be used in the practice of this invention.

OBJECTS OF THE INVENTION

It is therefore an object of the invention to provide a process and system to produce DRI with a controlled amount of chemically combined carbon, using a syngas with a low content of $CH_4$.

It is another object of the invention to produce a DRI carburizing gas within a process to produce DRI using a syngas with a low content of $CH_4$.

It is still another object of the invention to provide a process and system to produce DRI with a relatively high content of combined carbon which is discharged at high temperature from a reduction reactor using syngas with a low content of methane.

It is a further object of the invention to provide a process and system to produce DRI with a relatively high content of combined carbon which is discharged at low temperature from a reduction reactor using syngas with a low content of methane.

Other objects of the invention will be evident to those skilled in the art, or will be pointed out in the detailed description of the invention.

SUMMARY OF THE INVENTION

The objects of the invention are generally achieved by a process for reducing iron-oxides-containing feedstocks by a reducing gas comprising hydrogen and carbon monoxide at a temperature from about 750° C. to 1050° C. in a reduction reactor comprising a reduction zone, a lower discharge zone and a transition zone between said reduction zone and said lower discharge zone, said process comprising feeding a syngas, as a first gas stream, comprising $H_2$ and CO to a methane-forming reactor to convert $H_2$ and CO to $CH_4$, to produce a carburizing second gas stream containing more than about 20% of $CH_4$; and introducing said carburizing gas stream to the transition zone and/or to the lower discharge zone of said reactor.

The objects of the invention are generally achieved by a system for reducing iron-oxides-containing feedstocks comprising a vessel containing DRI at a temperature above 400° C.; a methane forming reactor containing a catalyst bed where $CH_4$ is produced from CO, $CO_2$ and $H_2$ resulting in a $CH_4$ rich gas stream; a first conduit to feed a gas stream comprising CO, $CO_2$ and $H_2$ to said methane forming reactor; and a second conduit to feed said $CH_4$ rich gas stream to said with said DRI. In one aspect of the invention, the vessel containing DRI is a direct reduction reactor.

DETAILED DESCRIPTION OF PREFERRED EMBODIMENTS OF THE INVENTION

Figure 1:
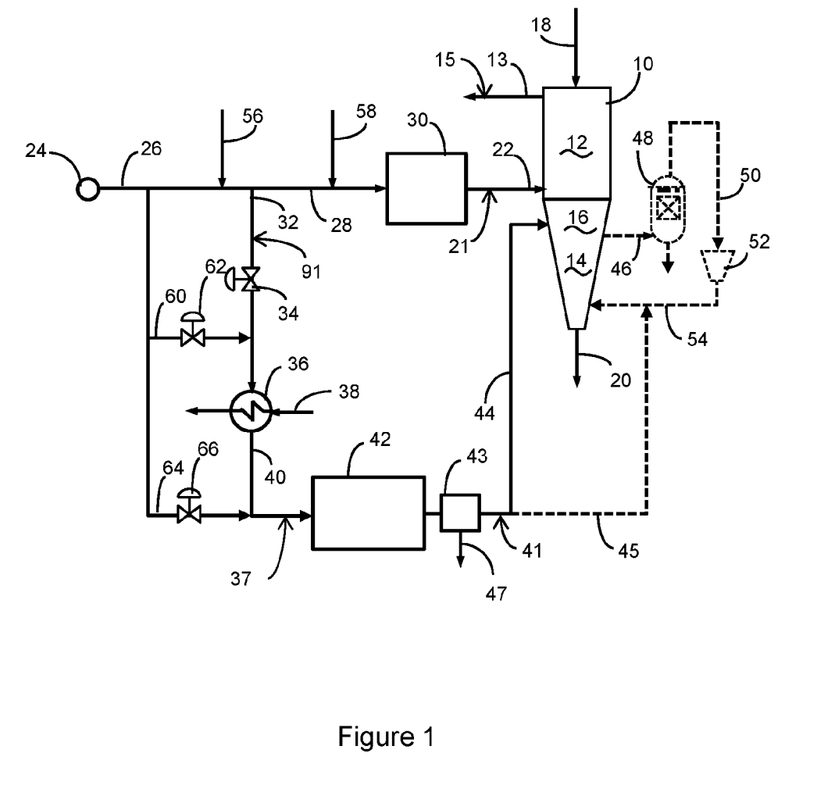
FIG. 1 shows an exemplary schematic illustration of a general block diagram of the process and system according to the invention for producing DRI with a controlled and high content of chemically combined carbon.
Figure 2:
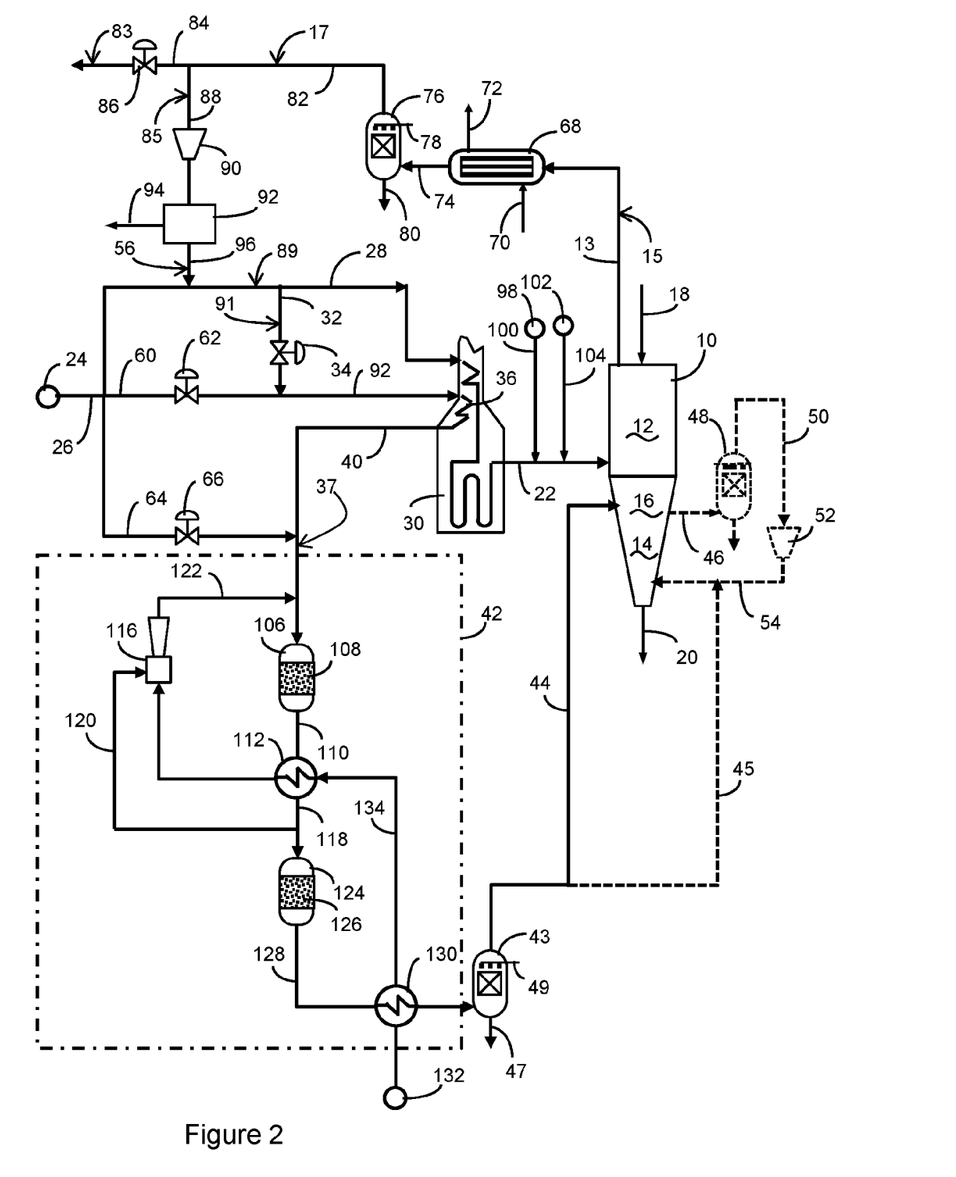
FIG. 2 shows an exemplary optional schematic and more detailed illustration of a process according to the invention and an optional system for producing DRI with a high carbon content.

For easier reference, the elements that are common in FIGS. 1 and 2 are designated by the same numerals.

Referring to FIG. 1 showing a general block diagram of an embodiment of the invention, numeral 10 generally designates a direct reduction reactor where iron-bearing materials 18, typically iron ore pellets containing iron oxides, are charged into a reduction zone 12 located in the upper part of said reduction reactor 10, which after having been reduced to metallic iron are discharged as direct reduced iron (DRI) 20 from the lower zone 14 of the reduction reactor 10.

Between reduction zone 12 and lower zone 14, there is a transition zone 16 where the DRI produced in reduction zone 12 continues descending at high temperature towards a discharge outlet located at the bottom of said lower zone 14.

The reducing gas 21 fed to the reduction zone 12 for reducing the iron oxides is mainly composed of $H_2$ and CO and also contains small amounts of $CH_4$, $CO_2$, $N_2$ and $H_2O$. This reducing gas flows via conduit 22 after it is heated to a suitable reduction temperature in the range between about 750° to 1050° C. in a gas heating device 30. The gas heating device 30 may comprise one or several heating devices; for example a tubular gas heater, a heat exchanger using waste heat from other hot streams of the reduction system or the steelmaking plant, or combustion chambers with oxygen or oxygen enriched air, refractory filled stoves of the regenerative type, electrical heaters, or combinations of these heating devices.

The heated reducing gas 21 exiting from gas heating device 30 enters the lower part of the reduction zone 12 and flows upwardly counter-currently to the downwardly descending moving bed of iron oxides pellets 18 and exits the reduction zone 12 through conduit 13 as a depleted reducing gas effluent 15. Typically, a portion of this reacted reducing gas 15 is recycled to reactor 10 after it is upgraded in its reduction potential by removing $H_2O$ and $CO_2$, which are by-products of the reduction reactions, and such upgraded reducing gas effluent may be added to the reducing gas stream 21 which will be fed to the reduction zone 12, through conduit 56 or conduit 58 to be heated in gas heating device 30 along with make-up reducing gas from source 24.

As mentioned before, chemically-combined carbon, mainly $Fe_3C$, may be obtained by two main chemical reactions: (a) by high temperature cracking of a hydrocarbon, typically $CH_4$, at a temperature above 400° C. which produces elemental carbon and $H_2$; and (b) by reaction of CO with $H_2$ to produce elemental carbon and $H_2O$, according to the following reactions:

$$CH_4 \rightarrow C+H_2 \quad (a)$$

$$CO+H_2 \rightarrow C+H_2O \quad (b)$$

The invention provides a practical and economical solution to the technical problem of utilizing a syngas having a low content of $CH_4$ or other hydrocarbons (which is the case when syngas is produced by partial oxidation of solid or liquid hydrocarbons such as coal and heavy oil) as the source of the reducing gas to operate a reduction reactor for the production of high-carbon DRI. The high temperature reached in a gasifier which is typically above about 1200° C. destroy almost all of the hydrocarbon molecules, including $CH_4$, and therefore the resulting syngas contains only about 1% to 5% of $CH_4$ after cleaning, after treatment in a catalytic water gas shift reactor to convert CO & $H_2O$ to $CO_2$ & $H_2$ and thus increase the ratio of $H_2$ to CO, and after removing $CO_2$ therefrom in order to increase the reduction potential of the gas to be fed to the reduction reactor.

The invention comprises the combination of a methane-forming reactor 42 with a reduction reactor 10 whereby syngas from source 24 comprising $H_2$, CO and $CO_2$ in variable proportions but containing not more than about 5% of $CH_4$, some $N_2$ and $H_2O$ is used as the source of reducing gas for reduction of iron oxides in reactor 10. The main flow of syngas is through conduits 26 and 28 to gas heating device 30, where it is heated to a temperature suitable to carry out the reduction of iron oxides, e.g. above 850° C., preferably above 950° C. and more preferably above 1020° C., and is then fed to the reduction zone 12 as the main part of the high-temperature reducing gas stream 21 as described above. Spent reducing gas 15 withdrawn through conduit 13 from the reduction zone 12 may be recycled through conduit 56 or conduit 58 to be included in the reducing gas stream 21, after having been treated to upgrade its reduction potential by removing $H_2O$ and $CO_2$ therefrom.

A portion 91 of syngas flowing through conduit 26 is diverted through conduit 32 provided with valve 34 and is heated in heat exchanger 36 by means of a hot stream 38 to a temperature in the range between 300° C. and 350° C. and then flows through conduit 40 to a methane forming reactor 42 where $H_2$ and CO and $CO_2$ contained in said syngas react to form $CH_4$ resulting in a $CH_4$ rich gas stream 41.

Preferably, the ratio on a volume basis of $H_2/(CO+CO_2)$ in the gas fed to the methane forming reactor is in the range between 2.5 and 3.5.

The $CH_4$ rich gas stream 41, after passing through a water removal unit 43 to eliminate water through conduit 47 which is produced by the methanation reactions (e) and (0, flows through conduit 44 and is fed to the transition zone 16 of reduction reactor 10 where the DRI is still at a temperature above 400° C., preferably in the order of 600° C. to 700° C. $CH_4$ reacts with the hot DRI in the transition zone 16 thus increasing the chemically combined carbon content of the DRI.

The heat exchanger 36 where the temperature of the syngas is raised to 250° C.-350° C. may be of any suitable type or structure. For example, the hot stream fed through conduit 38 may be combustion gases and the heat exchanger a tubular gas heater, or the hot stream may be off-gas withdrawn from the reduction zone of the reduction reactor, or other hot fluid stream from the reduction plant or steelmaking plant.

In another aspect of the invention, when DRI is discharged cold from the reduction reactor 10, a cooling gas is circulated through the bed of DRI in the lower part of the reactor 10, where it contacts DRI at a temperature above about 700° C. The cooling gas forms a cooling gas circuit (shown in dotted lines to indicate that it is an alternative embodiment) comprising the lower discharge zone 14, a conduit 46 through which the gas withdrawn from said zone 14 flows to a gas cooler 48, a conduit 50, a compressor 52 and a conduit 54 to feed the cooling gas to the lower discharge zone 14. The $CH_4$ rich gas stream 41 flows through conduit 45 and is fed to the lower discharge zone 14 where $CH_4$ reacts with the hot DRI thus increasing the carbon content of the DRI.

The content of carbon in the DRI is controlled by regulating the flow rate of the $CH_4$ rich gas stream 41 fed to the transition zone 16 or to the lower discharge zone 14.

In another exemplary embodiment of the invention, syngas from source 24 may also flow through conduit 60 provided with valve 62 directly to heat exchanger 36 without being combined with the recycled gas added though conduit 56. Choice of this alternative will depend on the actual composition of the syngas, taking into account that a certain amount of oxidants as $CO_2$ and/or $H_2O$ are required to avoid soot formation in the $CH_4$ forming reactor 42, and an adequate ratio of volume concentration of $H_2/(CO+CO_2)$ in the range between 2.5 and 3.5.

Also, if the syngas from source 24 is already available at a temperature between 300° C. and 350° C. and with an adequate composition, it may be fed through conduit 64 provided with valve 66 to $CH_4$ forming reactor 42, alone or combined with heated syngas effluent from heat exchanger 36.

Referring to FIG. 2, showing a more detailed embodiment of the invention and where the same numerals designate the same elements represented in FIG. 1, spent reducing gas 15 withdrawn from reduction zone 12 flows through conduit 13 to a heat exchanger 68 where heat is transferred to a fluid stream 70 which exits as hot fluid stream 72 and the partially cooled spent reducing gas is then led through conduit 74 to gas cooler 76 where water 78 cools down the gas and exits through conduit 80 along with condensed water from said spent reducing gas. The cooled and dewatered gas 17 flows through conduit 82 to be recycled to the reduction reactor 10 in a reducing gas circuit, after a minor portion of gas 17 is purged from the reduction system through conduit 84 provided with pressure regulating valve 86 which regulates the pressure of the reduction system. The gas 83 purged through conduit 84 also serves the purpose of preventing inert gases, as nitrogen from accumulating in the reducing gas circuit.

The dewatered recycled reducing gas 85 flows through conduit 88 to compressor 90 and then to a $CO_2$ removal unit 92 where $CO_2$ is removed from the recycled reducing gas 85 through $CO_2$-removal conduit 94 upgrading its reduction potential after the products of the reduction reactions $CO_2$ and $H_2O$ have been removed therefrom. This $CO_2$ removal unit 92 may be a chemical absorption system using an amine or mixtures of amines liquid solution to react with the $CO_2$ present in the recycled gas or it may be of the physical adsorption of the Pressure Swing Adsorption (PSA) or Vacuum Pressure Swing Adsorption (VPSA) or of the molecular membranes in a manner known in the art.

The thus upgraded recycled gas 56 flows through conduit 96 and on to heater 30 via conduit 28 after being mixed with a stream of syngas from source 24 where it is heated to a temperature suitable for reduction of iron oxides in the range from 850° C. to 1100° C., preferably between 950° C. and 1050° C., and is thereafter directed through conduit 22 to the reduction zone 12 to reduce the iron oxides and produce DRI. Oxygen of industrial purity, or oxygen enriched air, may be injected from source 98 through conduit 100 to further raise the temperature of the reducing gas stream in conduit 22 by partial combustion thereof and also a hydrocarbon-containing gas from source 102, which can be syngas from source 24, natural gas, coke oven gas or other hydrocarbon-containing gas available, through conduit 104 to contribute in the partial combustion with oxygen to raise the temperature of the reducing gas and/or adjust the composition of the reducing gas as desired. The oxygen-containing gas 98 and the hydrocarbon-containing gas 102 may be added to the gas stream flowing through conduit 22 separately or together through a combustion chamber.

A portion 91 of the gas stream 89 resulting from the mixture of syngas 24 and recycled reducing gas flowing through conduit 28 is diverted through conduit 32 provided with valve 34, and this gas stream 91 is preheated in heating section 36 of heater 30 to a temperature between 300° C. and 350° C. and is led through conduit 40 to a first methane forming reactor 106 having a first bed of catalyst 108 where CO and $CO_2$ and $H_2$ react to form $CH_4$. Since this reaction is exothermic, the hot gas effluent from reactor 106 through conduit 110 passes through a heat exchanger 112. Steam is used in ejector 116 to recirculate a portion of the gas flowing through conduit 118 by means of conduit 120 which after being mixed with the steam flows through conduit 122, thus increasing the content of water in the gas to avoid soot formation in catalyst bed 108. The partially reacted gas from reactor 106 then passes through a second methane forming reactor 124 having a second bed of catalyst 126 where the $CH_4$ content is increased, and after flowing through conduit 128 and being cooled in heat exchanger 130, it flows on to gas cooler 43 (where condensed water is withdrawn through conduit 47 along with the water used for the gas cooling fed at 49). After water separation, the $CH_4$ rich gas stream 41 flows though conduit 44 and is then used as a DRI carburizing gas with a $CH_4$ content above 20% by volume in transition zone 16 or alternately flows through conduit 45 and is used as carburizing gas in the lower discharge zone 14 of reduction reactor 10.

If the syngas from source 24 is available at a temperature between 300° C. and 350° C., it may be fed through conduit 64 provided with valve 66 to $CH_4$ forming reactor 42, alone or combined with heated syngas effluent from heat exchanger 36.

The heat transferred from the $CH_4$ rich gas stream in heat exchanger 130 is used to preheat water from source 132 that is led through conduit 134 to heat exchanger 112 for steam production which is used in ejector 116 to recycle gas effluent from the first catalyst bed 108 and thereby adjust the composition of the gas fed to said catalyst bed 108.

The invention may be practiced independently of the extent the methane forming reactions are carried out, as long as the $CH_4$ content in the carburizing gas fed to the transition zone or the lower discharge zone of the reactor is above 20% by volume.

As described above with reference to FIG. 1, the $CH_4$ rich gas stream 41 is circulated through the bed of DRI in the lower part of the reactor 10 as the carburizing gas and also as the cooling gas, where it contacts DRI at a temperature above about 700° C. The cooling gas forms a cooling gas circuit (shown in dotted lines to indicate that it is an alternative embodiment) comprising the lower discharge zone 14, a conduit 46 through which the gas withdrawn from said zone 14 flows to a gas cooler 48, a conduit 50, a compressor 52 and a conduit 54 to feed the cooling gas to the lower discharge zone 14. The $CH_4$ rich gas stream 41 flows through conduit 45 and is fed to the lower discharge zone 14 where $CH_4$ reacts with the hot DRI thus increasing the carbon content of the DRI.

The methane forming reactions may be carried out, within the scope of the invention, in an isothermic methane forming reactor, in an adiabatic reactor or in a combination of isothermic and adiabatic reactors, producing a $CH_4$ rich carburizing gas useful for producing high carbon DRI.

Example 1

A syngas stream 24 derived from the gasification of coal combined with an upgraded reducing gas stream effluent received via conduit 56 from the reduction zone 12 of a reduction reactor 10 having a composition in % by volume as follows: $H_2$: 66.435; CO 19.025; $CO_2$: 4.919; $CH_4$: 2.431; $N_2$: 5.208 and $H_2O$: 2.0 is fed as stream 37 to an isothermic methane-forming reactor 42 producing a $CH_4$ rich gas stream 41 with the following composition after most of the water (byproduct of the methanation reactions) has been removed therefrom: $H_2$: 3.627; CO 0.850; $CO_2$: 8.587; $CH_4$: 71.550; $N_2$: 15.826 and $H_2O$: 1.0. By feeding 20,000 NCMH of this $CH_4$ rich gas stream 41 to the transition zone 16 of a reduction reactor 10 producing 100 tons of DRI per hour, the DRI carbon content is about 2.0% by weight in average. Increasing the flow rate of the $CH_4$ rich gas stream 41 to the transition zone 16 for example to 40,000 NCMH, the DRI is produced with a carbon content of 4.0%.

Example 2

A syngas stream 24 derived from the gasification of coal combined with an upgraded reducing gas stream effluent received via conduit 56 from the reduction zone 12 of a reduction reactor 10 having a composition in % by volume as follows: $H_2$: 66.435; CO 19.025; $CO_2$: 4.919; $CH_4$: 2.431; $N_2$: 5.208 and $H_2O$: 2.0 is fed as stream 37 to an adiabatic methane forming reactor 42 producing a $CH_4$ rich gas stream 41 with the following composition after most of the water (byproduct of the methanation reactions) has been removed therefrom: $H_2$: 27.308; CO 0.122; $CO_2$: 12.59; $CH_4$: 47.16; $N_2$: 11.820 and $H_2O$: 1.0. By feeding 23,000 NCMH of this $CH_4$ rich gas stream 41 to the transition zone 16 of a reduction reactor 10 producing 100 tons of DRI per hour, the DRI carbon content is 2.0% by weight in average. Increasing the flow rate of the $CH_4$ rich gas stream 41 to the transition zone 16 for example to 46,000 NCMH, the DRI is produced with a carbon content of 4.0%.

It is of course to be understood that in this specification only some preferred embodiments of the invention have been described for illustration purposes and that the scope of the invention is not limited by such described embodiments but only by the scope of the appended claims.

What is claimed is:

1. A process for producing direct reduced iron (DRI) having chemically-combined carbon in a direct reduction reactor for the production of said DRI, said direct reduction reactor having at least a reduction zone, a lower zone, and a transition zone between said reduction zone and said lower zone, the process comprising:
   providing a first portion of a first gas stream comprising hydrogen and carbon monoxide to said reduction zone, said first gas stream being a syngas with less than 5 vol % methane, to produce said DRI in said reduction zone;
   providing said DRI at a temperature above 400° C. to said transition zone, said lower zone, or both;
   passing a second portion of said first gas stream through a methane-forming reactor where methane is produced from said hydrogen and carbon monoxide resulting in a second gas stream containing a higher concentration of methane than said first gas stream; and
   contacting said second gas stream with said DRI in said transition zone, said lower discharge zone, or both to increase the carbon content of said DRI in said transition zone, said lower zone, or both, respectively.

2. A process for producing DRI having a controlled amount of chemically-combined carbon, according to claim 1, wherein said first gas stream contains hydrogen, carbon monoxide and carbon dioxide and wherein the ratio of $H_2/(CO+CO_2)$ in the gas fed to the methane forming reactor is in the range between 2.5 and 3.5.

3. A process for producing DRI having a controlled amount of chemically-combined carbon, according to claim 1, wherein said second gas stream contains at least 20% by volume of methane.

4. A process for producing DRI having a controlled amount of chemically-combined carbon, according to claim 1, wherein said methane forming process is performed isothermically.

5. A process for producing DRI having a controlled amount of chemically-combined carbon, according to claim 1, wherein said methane forming process is performed adiabatically.

6. A process for producing DRI having a controlled amount of chemically-combined carbon, according to claim 1, wherein said methane forming process comprises a combination of isothermic and adiabatic methane forming processes.

7. A process for producing DRI having a controlled amount of chemically-combined carbon, according to claim 1, wherein said first gas stream fed to the methane forming process is syngas derived from gasification of hydrocarbons.

8. A process for producing DRI having a controlled amount of chemically-combined carbon, according to claim 7, wherein said first gas stream of syngas is reacted with $H_2O$ to increase its content of $H_2$ and $CO_2$ in a catalytic water gas shift reactor prior to being fed to said methane forming process.

9. A process for producing DRI having a controlled amount of chemically-combined carbon, according to claim 8, wherein the syngas from said catalytic water gas shift reactor is treated in a $CO_2$ removal unit.

10. A process for producing DRI having a controlled amount of chemically-combined carbon, according to claim 9, wherein said $CO_2$ removal unit is of the chemical absorption type.

11. A process for producing DRI having a controlled amount of chemically-combined carbon, according to claim 9, wherein said $CO_2$ removal unit is of the physical adsorption type or gas separation membranes.

12. A process for producing DRI having a controlled amount of chemically-combined carbon, according to claim 1, wherein said first gas stream containing hydrogen and carbon monoxide is syngas from a coal gasifier.

13. A process for producing DRI having a controlled amount of chemically-combined carbon, according to claim 1, wherein said first gas stream containing hydrogen and carbon monoxide is a combination of syngas from a coal gasifier and recycled upgraded reducing gas effluent from a direct reduction reactor.

14. A process for producing DRI having a controlled amount of chemically-combined carbon, according to claim 1, wherein said second gas stream is fed to the transition zone of the direct reduction reactor.

15. A process for producing DRI having a controlled amount of chemically-combined carbon, according to claim 1, wherein said second gas stream is fed to a lower zone of a direct reduction reactor.

16. A process for producing DRI having a controlled amount of chemically-combined carbon, according to claim 1, wherein a cooling gas stream is circulated through said lower zone of the direct reduction reactor and said second gas stream is fed to the cooling gas circuit comprising said lower zone of the direct reduction reactor.

17. A process for producing DRI having a controlled amount of chemically-combined carbon, according to claim 1, wherein said DRI contains 2% by weight or more of combined carbon.

18. A process for producing DRI having a controlled amount of chemically-combined carbon, according to claim 1, wherein said DRI contains from 2% by weight to 4.5% by weight of combined carbon.

19. A process for producing DRI having a controlled amount of chemically-combined carbon, according to claim 1, wherein said second gas stream is treated to remove water before contacting said DRI.

20. A system for producing direct reduced iron (DRI) having chemically-combined carbon, the system comprising:
   a direct reduction reactor for the production of said DRI having at least a reduction zone, a lower zone, and a transition zone between the reduction zone and the lower zone, said transition zone, said lower zone, or both containing DRI at a temperature above 400° C.;
   a methane forming reactor containing a catalyst bed for producing methane from a first portion of first gas stream containing hydrogen and carbon monoxide resulting in a second gas stream having a higher content of methane than said first gas stream;

a first conduit to feed the first portion of the first gas stream to said methane forming reactor;

a second conduit to feed said second gas stream to said transition zone, said lower zone, or both; and a third conduit to feed a second portion of the first gas stream to the direct reduction reactor for the production of said DRI.

21. A system for producing DRI according to claim 20, further comprising a water removal unit fluidly connected with said methane forming reactor and with said transition zone, said lower zone, or both.

22. A system for producing DRI according to claim 21, further comprising a source of syngas containing less than 10% methane as source of said first gas stream.

23. A system for producing DRI according to claim 22, wherein said source of syngas is a coal gasifier.

24. A system for producing DRI according to claim 22, wherein said source is a coal gasifier comprising a gas cleaning system to lower the sulfur content of the gas stream.

25. A system for producing DRI according to claim 21, further comprising a conduit to feed at least a portion of said methane containing second gas stream from said water removal unit to said transition zone.

26. A system for producing DRI according to claim 21, further comprising a conduit to feed at least a portion of said methane containing second gas stream from said water removal unit to said lower zone.

* * * * *

UNITED STATES PATENT AND TRADEMARK OFFICE
CERTIFICATE OF CORRECTION

PATENT NO. : 10,927,424 B2  
APPLICATION NO. : 16/063604  
DATED : February 23, 2021  
INVENTOR(S) : Eugenio Zendejas-Martinez Page 1 of 1

It is certified that error appears in the above-identified patent and that said Letters Patent is hereby corrected as shown below:

On the Title Page

Column 1 (Assignees), Line 1, delete "S. A." and insert -- S.A. --

Column 1 (Assignees), Line 3, delete "MECCANICHE" and insert -- MECCANICHE, --

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*